US00PP27863P3

(12) United States Plant Patent
Randag

(10) Patent No.: US PP27,863 P3
(45) Date of Patent: Apr. 4, 2017

(54) CALLA LILY PLANT NAMED 'ORANGE COUNTY'

(50) Latin Name: *Zantedeschia sprengeri*
Varietal Denomination: Orange County

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 51 days.

(21) Appl. No.: 14/544,313

(22) Filed: Dec. 22, 2014

(65) Prior Publication Data

US 2015/0296684 P1 Oct. 15, 2015

Related U.S. Application Data

(60) Provisional application No. 61/964,771, filed on Jan. 14, 2014.

(51) Int. Cl.
*A01H 5/02* (2006.01)

(52) U.S. Cl.
USPC ..... Plt./490

(58) Field of Classification Search
USPC ..... Plt./490
See application file for complete search history.

*Primary Examiner* — Susan McCormick Ewoldt
(74) *Attorney, Agent, or Firm* — The Webb Law Firm

(57) ABSTRACT

'Orange County' is a new variety of calla lily having inflorescences with an orange-red colored spathe that produces 4-18 inflorescences per tuber. The inflorescence stems are about 30 cm in height, and the leaves are green with whitish spots and have a leathery texture.

2 Drawing Sheets

Botanical classification: *Zantedeschia sprengeri.*
Varietal denomination: 'ORANGE COUNTY'.

BACKGROUND OF THE NEW PLANT

The present invention comprises a new and distinct cultivar of calla lily, botanically known as *Zantedeschia sprengeri* and hereinafter referred to by the cultivar name 'Orange County'.

'Orange County' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of *Zantedeschia sprengeri* 'Mercedes' (female parent, unpatented) with a *Zantedeschia sprengeri* seedling referred to as Z050986-7120 (male parent, unpatented). 'Orange County' was selected in 2009 by the inventor in 't Zand, The Netherlands as one flowering plant within the progeny of the stated cross.

The first act of asexual reproduction of 'Orange County' by tissue culture was performed by the inventor in September of 2009 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in a 14 cm pot at 12-14 weeks after planting in 't Zand, The Netherlands under greenhouse conditions, which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Orange County' which, in combination, distinguish this calla lily as a new and distinct cultivar:

1. Intense orange-red colored spathe;
2. Compact growth habit; and
3. High inflorescence production.

Further, when compared to calla lily plant named 'Orania' (pending U.S. Plant patent application Ser. No. 14/544,444), both varieties have an upper surface spathe color that varies between Orange Group RHS 25A and 25B. However, the lower surface spathe color of 'Orania' varies between Yellow Group RHS 7A and 7B with an under margin ending in Orange-Red Group RHS 34A to 34B, while the lower surface spathe color of 'Orange County' varies between Yellow-Orange Group RHS 19A and 19B.

Table 1 provides similarities and differences of 'Orange County' to its parents, *Zantedeschia sprengeri* 'Mercedes' and seedling Z050986-7120.

TABLE 1

| 'Orange County' | Similarities | Differences |
|---|---|---|
| 'Mercedes' | Spathe shape | Spathe color (Upper and lower surface is between Red Group RHS 46C and 46D) |
| | Plant height | Number of inflorescences (2-15) |
| | | No white spots on leaves |
| Z050986-7120 | Leaf shape | Spathe shape (Funnel) |
| | Plant height | Spathe color (Between Orange Group RHS N25B and 26B) |
| | | Number of inflorescences (3-12) |

BRIEF DESCRIPTION OF THE DRAWINGS

The accompanying photographic drawings illustrate the new variety at 12-14 weeks after planting, with the colors being as nearly true as is possible with color illustrations of this type.

DESCRIPTION OF THE PLANT

The Plant

Figure 1:
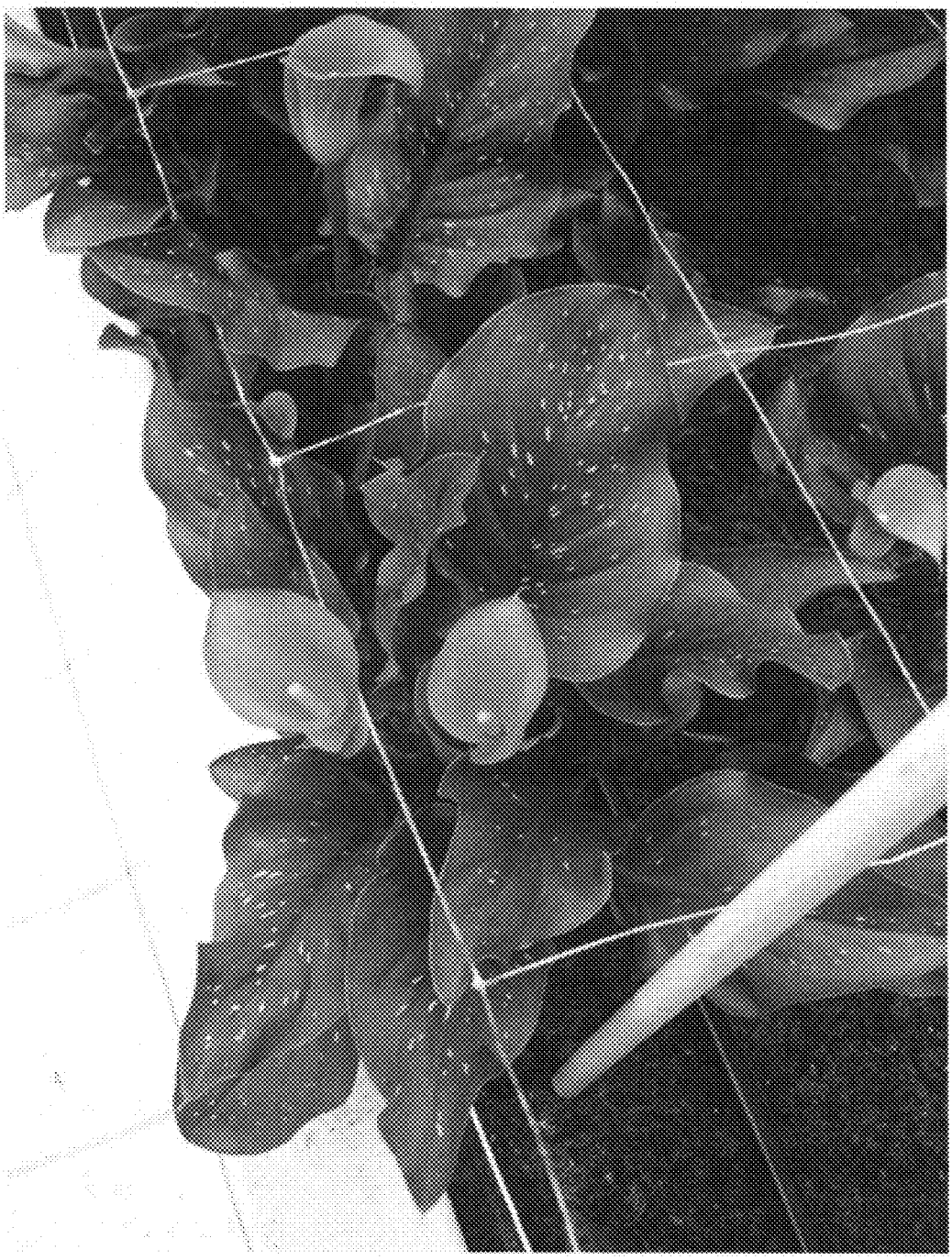
FIG. 1 is a photograph of an overhead view of a plant of the new variety.
Figure 2:
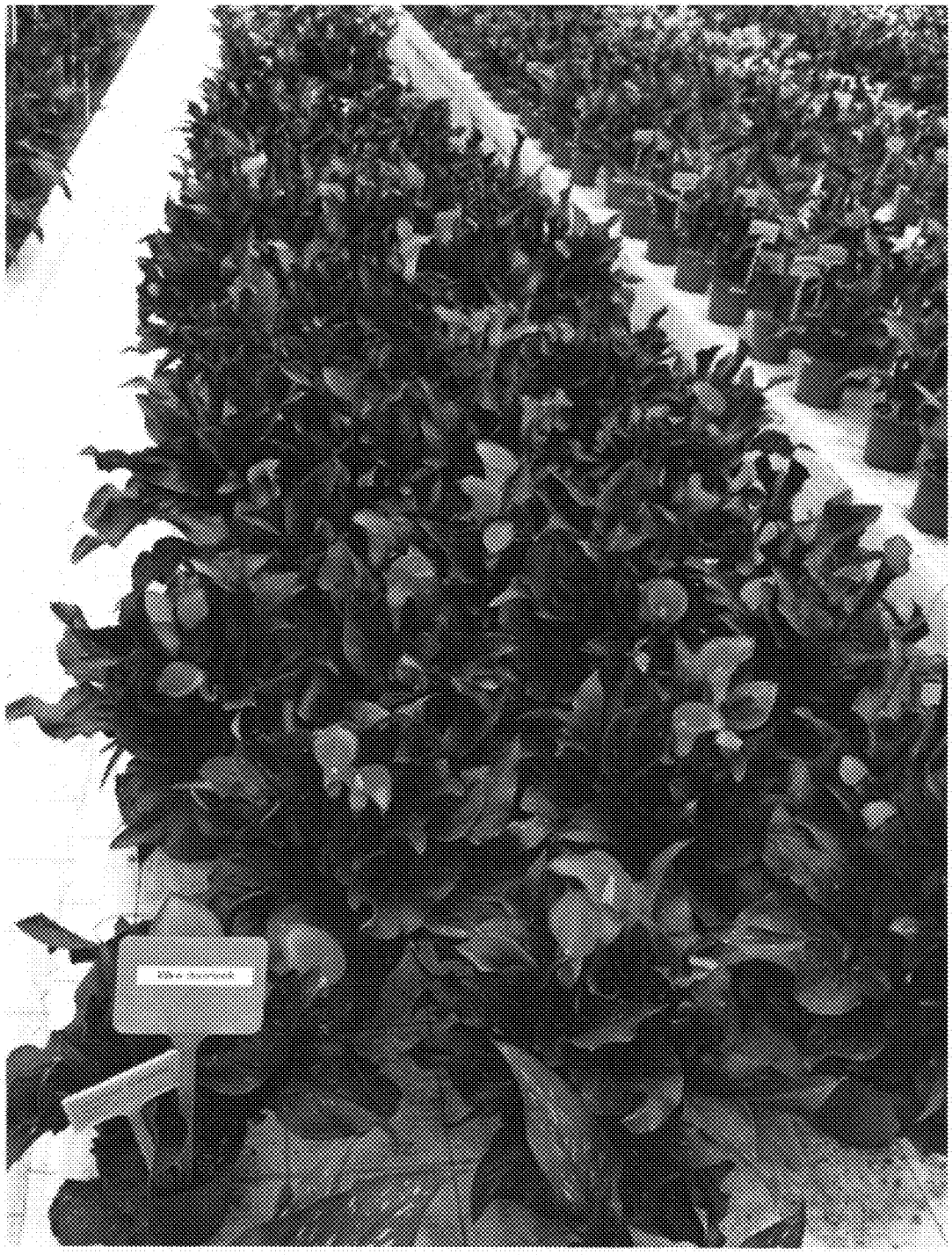
FIG. 2 is a photograph of a group of multiple plants of the new variety.

Size:

*Height of the leaf canopy above the soil.*—7-35 cm.

*Height of top of inflorescence above the soil.*—17-35 cm.

*Diameter.*—20-40 cm.

Form: Erect.

Number of inflorescences per tuber:

*Size* 14-16 *cm in diameter.*—5-8 inflorescences.

*Size* 16-18 *cm in diameter.*—6-12 inflorescences.

*Size* 18-20 *cm in diameter.*—7-18 inflorescences.

Branches:

*Character.*—Many (3-9); like the variety 'Odessa' (U.S. Plant Pat. No. 18,833).

*Color.*—Between Green Group RHS 137A to 137B.

Leaves:

*Size.*—Width: 3-12 cm. Length: 5-20 cm.

*Number per plant.*—18-26.

*Shape.*—Lanceolate.

*Color.*—Upper surface: Green Group RHS 137A to 137B, with transparent White Group RHS 155A and N155A spots. Lower surface: Green Group RHS 138A to 138B, with transparent White Group RHS 155A and N155A spots.

*Apex.*—Apiculate.

*Base.*—Truncate.

*Margin.*—Undulate; having a color of Green Group RHS 137A to 137B.

*Veins.*—Configuration: Pinnate. Color: Green Group RHS 143A to 143B.

*Surface quality.*—Leathery.

*Petiole.*—Length: 7-18 cm. Diameter: 10 mm. Color: The base is White Group RHS 155A, and the upper part is Green Group RHS 143A to 143B.

Roots:

*Color.*—White.

*Branching.*—Similar to other *Zantedeschia* varieties.

The Inflorescence and Seeds

Spathe:

*Size.*—Length (measured from base opening to tip): 3-7 cm. Width: 3-6 cm. Height: 3-8 cm.

*Color.*—Upper surface: Varies between Orange Group RHS 25A and 25B. Lower surface: Varies between Yellow-Orange Group RHS 19A and 19B.

*Vein color.*—Between Red Group RHS 46A and 46B.

*Shape.*—Cupped.

*Apex.*—Apiculate.

*Base.*—Apiculate.

*Texture.*—Smooth (upper and lower surfaces).

Spadix:

*Size.*—Length: 25-50 mm. Diameter: 3-12 mm.

*Color.*—Between Yellow-Orange Group RHS 17B and 17C.

*Position relative to spathe.*—Upright.

Peduncle:

*Size.*—Length: 8-28 cm. Diameter: 4-12 mm.

*Color.*—The upper part is between Yellow-Green Group RHS 144A and 144B, and the lower part is Green-White Group RHS 157C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 20. Pollen amount: Abundant and similar to 'Picasso' (U.S. Plant Pat. No. 15,282), but not quantifiable due to minute pollen size. Color: Between White Group RHS 155A and 155B.

*Anther.*—Shape: Round. Length: Less than 1 mm. Color: Between Yellow-Orange Group RHS 17B and 17C.

*Filament.*—Length: Less than 1 mm. Color: Between White Group RHS 155A and 155B.

*Pistil.*—Number: 15 to 30. Length beyond perianth: About 1 mm.

*Stigma.*—Shape: Round. Size: Less than 1 mm.

*Style.*—Length: Less than 1 mm. Color: Between Yellow Group RHS 13B and 13C.

*Ovaries.*—Texture: Smooth. Length: Between 1 to 10 mm. Width: Between 1 to 10 mm. Color: Top color is between Yellow-Green Group RHS 154A and 154B, bottom color is from White Group RHS 155B to 157C.

Seeds:

*Length.*—4-7 mm.

*Width.*—3-6 mm.

*Color.*—Between Yellow-Green Group RHS 150A and 151A.

*Amount.*—Between 1-60.

Fruit:

*Amount.*—Multiple berries produced.

*Shape.*—Irregular.

*Color.*—Varies between Yellow-Green Group RHS N144C to 145A.

General

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July. In general, the time from planting to first flowering takes eight weeks. However, tubers stored for a longer period before planting may flower earlier—up to five weeks after planting.

Lastingness: About two weeks on the plant.

Fragrance: None.

I claim:

1. A new and distinct variety of calla lily plant named 'Orange County' as herein described and illustrated.

* * * * *